United States Patent [19]
Kontos

[11] Patent Number: 6,132,439
[45] Date of Patent: Oct. 17, 2000

[54] KNOT PUSHER

[75] Inventor: Stavros Kontos, Woodcliff Lake, N.J.

[73] Assignee: X-Site, L.L.C., Totowa, N.J.

[21] Appl. No.: 09/250,298

[22] Filed: Feb. 17, 1999

[51] Int. Cl.$^7$ .................................................. A61B 17/10
[52] U.S. Cl. ........................................ 606/139; 606/148
[58] Field of Search .................... 606/139, 144, 606/148, 113, 103, 140; D24/145, 147

[56] References Cited

U.S. PATENT DOCUMENTS

| | | | |
|---|---|---|---|
| D. 353,002 | 11/1994 | Tovey ........................................ | D24/145 |
| D. 359,355 | 6/1995 | Ferragamo et al. .................... | D24/145 |
| D. 360,687 | 7/1995 | Ferragamo et al. .................... | D24/145 |
| D. 360,688 | 7/1995 | Ferragamo et al. .................... | D24/145 |
| D. 386,583 | 11/1997 | Ferragamo et al. .................... | D24/145 |
| D. 387,161 | 12/1997 | Ferragamo et al. .................... | D24/145 |
| 4,602,635 | 7/1986 | Mulhollan et al. ...................... | 128/334 |
| 5,129,912 | 7/1992 | Noda et al. ............................... | 606/139 |
| 5,176,691 | 1/1993 | Pierce ....................................... | 606/148 |
| 5,192,287 | 3/1993 | Fournler et al. ......................... | 606/139 |
| 5,217,471 | 6/1993 | Burkhart .................................. | 606/148 |
| 5,234,445 | 8/1993 | Walker et al. ............................ | 606/148 |
| 5,242,459 | 9/1993 | Buelna ..................................... | 606/148 |
| 5,269,791 | 12/1993 | Mayzels et al. .......................... | 606/148 |
| 5,284,485 | 2/1994 | Kammerer et al. ...................... | 606/148 |
| 5,292,327 | 3/1994 | Dodd et al. .............................. | 606/148 |
| 5,320,629 | 6/1994 | Noda et al. ............................... | 606/139 |
| 5,324,298 | 6/1994 | Phillips et al. ............................ | 606/148 |
| 5,330,491 | 7/1994 | Walker et al. ............................ | 606/148 |
| 5,391,175 | 2/1995 | Sharpe et al. ............................ | 606/148 |
| 5,397,326 | 3/1995 | Mangum .................................. | 606/148 |
| 5,403,330 | 4/1995 | Tuason .................................... | 606/148 |
| 5,403,331 | 4/1995 | Chesterfield et al. .................... | 606/148 |
| 5,423,837 | 6/1995 | Mericle et al. ........................... | 606/148 |
| 5,439,470 | 8/1995 | Li .............................................. | 606/148 |
| 5,454,820 | 10/1995 | Kammerer et al. ...................... | 606/148 |
| 5,454,821 | 10/1995 | Harm et al. .............................. | 606/148 |
| 5,466,241 | 11/1995 | Leroy et al. .............................. | 606/139 |
| 5,472,446 | 12/1995 | de la Torre .............................. | 606/148 |
| 5,549,618 | 8/1996 | Fleenor et al. ........................... | 606/148 |
| 5,562,684 | 10/1996 | Kammerer ............................... | 606/139 |
| 5,584,861 | 12/1996 | Swain et al. ............................. | 606/232 |
| 5,601,576 | 2/1997 | Garrison .................................. | 606/148 |
| 5,653,719 | 8/1997 | Ralken .................................... | 606/148 |
| 5,693,060 | 12/1997 | Martin ...................................... | 606/148 |
| 5,693,061 | 12/1997 | Pierce et al. ............................. | 606/148 |
| 5,704,943 | 1/1998 | Yoon et al. ............................... | 606/139 |
| 5,746,752 | 5/1998 | Burkhart .................................. | 606/139 |
| 5,752,964 | 5/1998 | Mericle .................................... | 606/148 |
| 5,759,189 | 6/1998 | Ferragamo et al. ..................... | 606/148 |
| 5,766,217 | 6/1998 | Christy .................................... | 606/148 |
| 5,769,862 | 6/1998 | Kammerer et al. ..................... | 606/148 |
| 5,769,863 | 6/1998 | Garrison .................................. | 606/148 |
| 5,776,150 | 7/1998 | Nolan et al. ............................. | 606/148 |
| 5,797,928 | 8/1998 | Kogasaka ................................ | 606/144 |
| 5,797,929 | 8/1998 | Andreas et al. ......................... | 606/148 |

FOREIGN PATENT DOCUMENTS

| | | | |
|---|---|---|---|
| 0 624 343 A2 | 11/1994 | European Pat. Off. ........ | A61B 17/04 |
| 0 706 779 A1 | 4/1996 | European Pat. Off. ........ | A61B 17/04 |
| 649416 | 2/1979 | U.S.S.R. ......................... | A61B 17/04 |
| 1169630 | 7/1985 | U.S.S.R. ......................... | A61B 17/04 |
| 2 198 951 | 6/1988 | United Kingdom ............. | A61C 7/00 |
| 2 247 841 | 3/1992 | United Kingdom ........... | A61B 17/04 |
| WO 96/04854 | 2/1996 | WIPO ............................. | A61B 17/04 |

*Primary Examiner*—Michael Buiz
*Assistant Examiner*—Lien Ngo
*Attorney, Agent, or Firm*—Kenyon & Kenyon

[57] ABSTRACT

A knot pusher according to the present invention includes a longitudinal member having a proximal end and a distal end, the longitudinal member having a suture slit extending along a portion of the longitudinal member from the distal end. In addition, the knot pusher includes a latch coupled to the distal end of the longitudinal member. The latch is movable between an extended position and a locking position, so that the latch obstructs a portion of the suture slit when in the locking position. A suture having a knot may be inserted within the latch and through the suture slit, and the latch may then be moved to the locking position. With the suture locked in the suture slit, an operator may run the knot down the length of suture to cinch the knot.

26 Claims, 4 Drawing Sheets

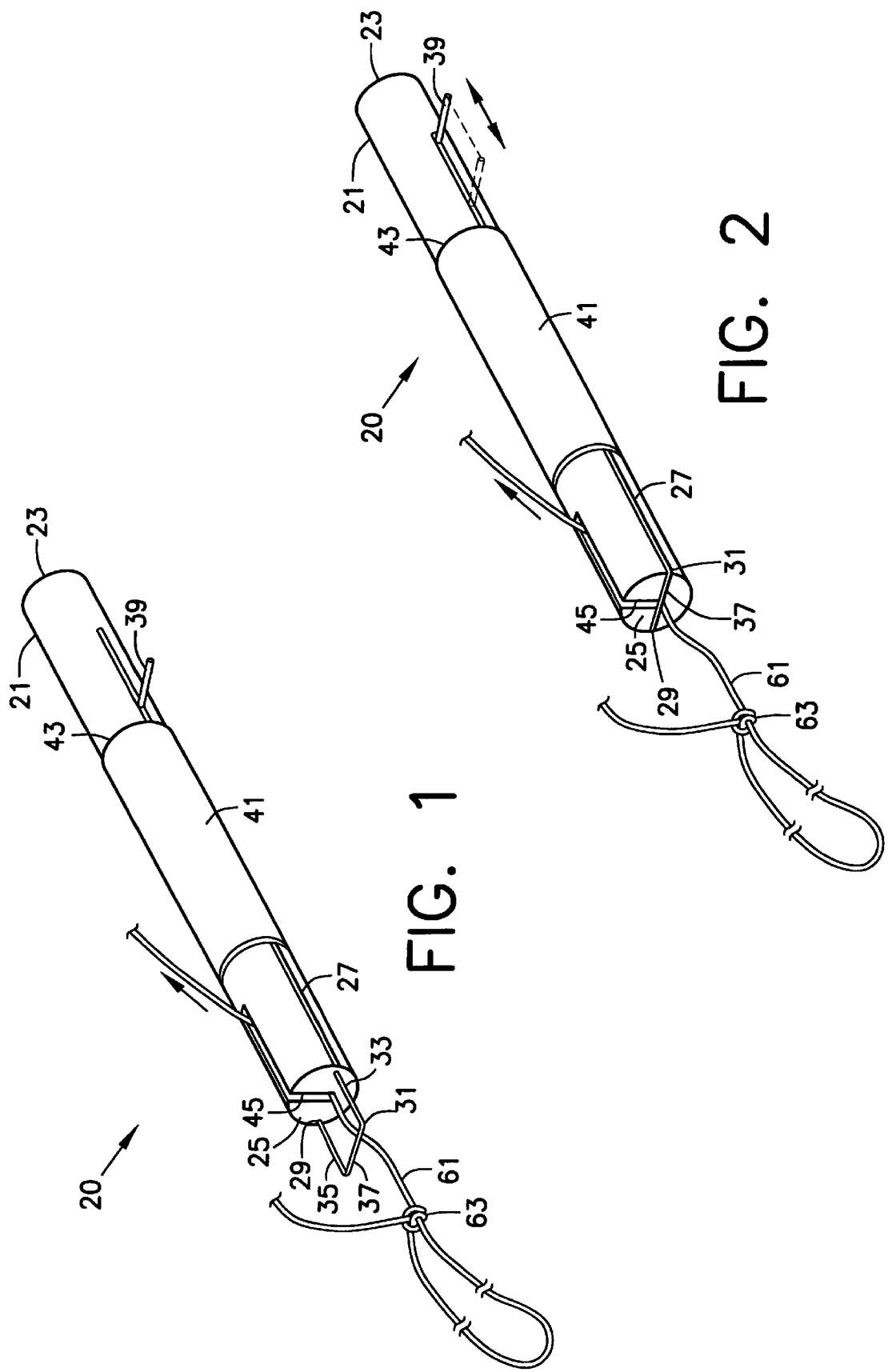

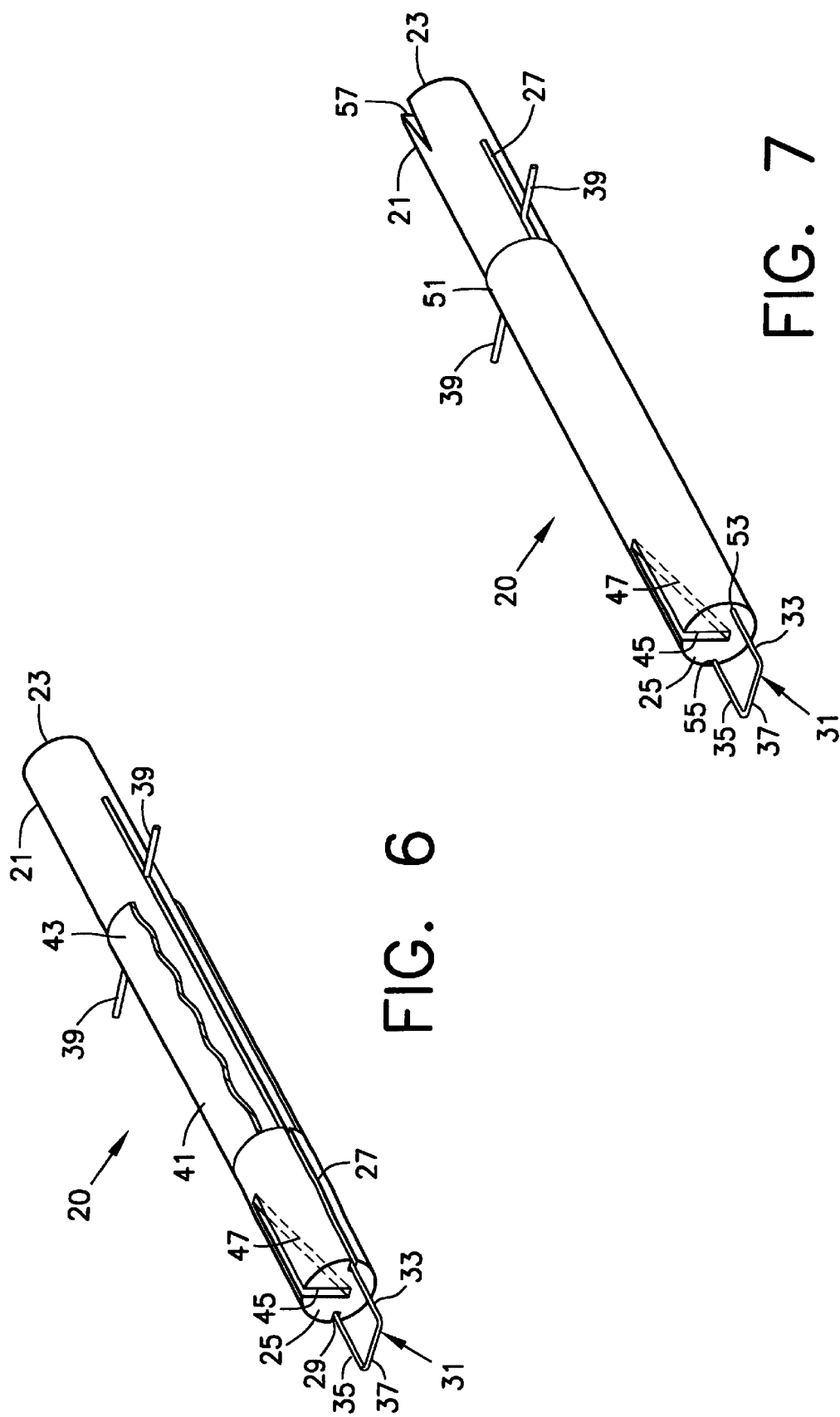

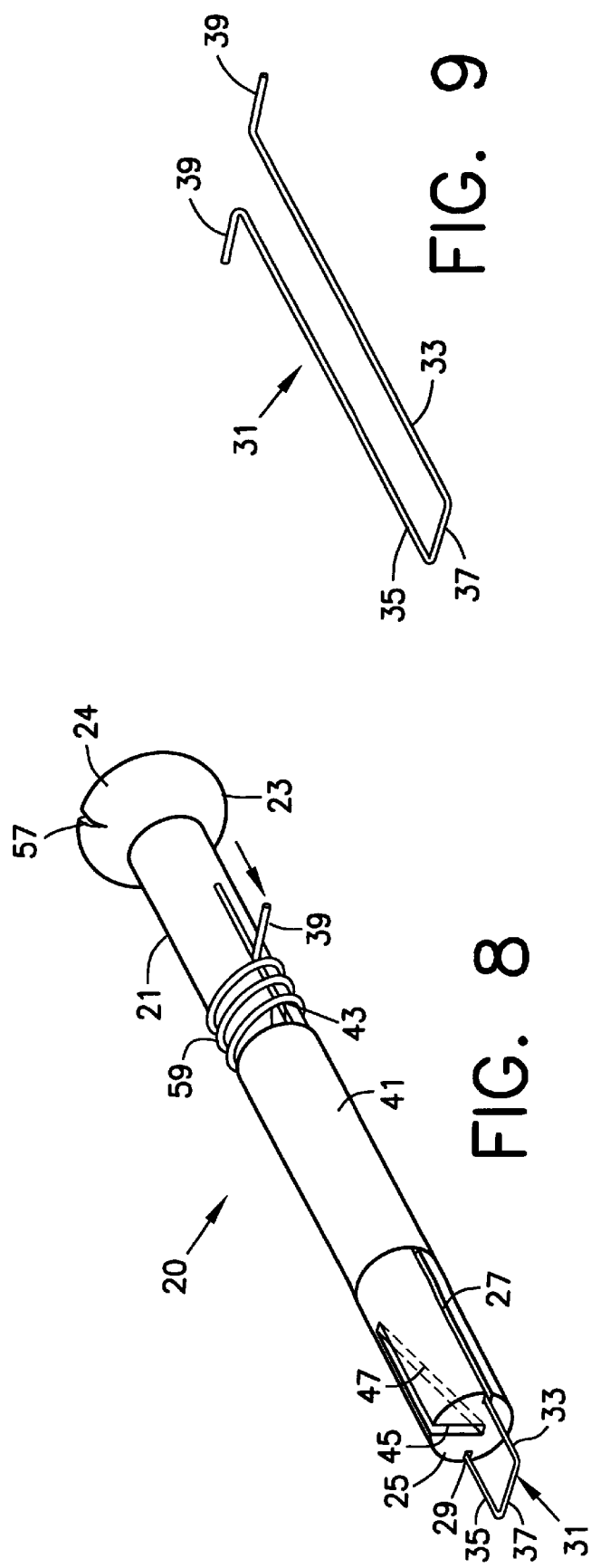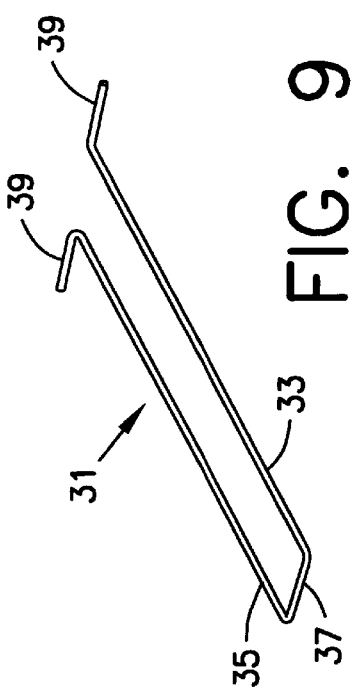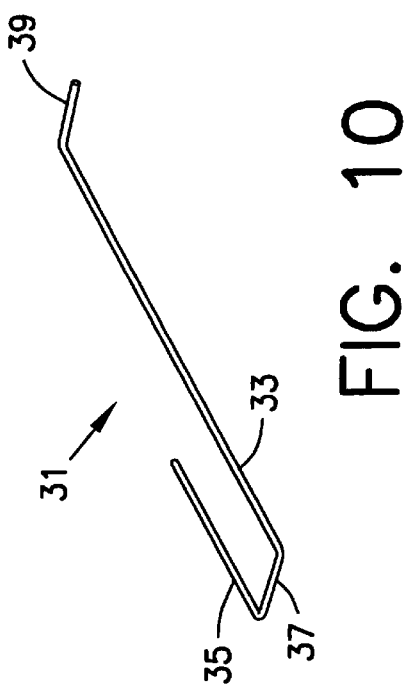

KNOT PUSHER

FIELD OF THE INVENTION

The present invention relates to surgical devices, and in particular to a device for tightening a suture knot, for example in conjunction with an endoscopic procedure.

BACKGROUND INFORMATION

In many surgical procedures, it is advantageous to close an incision or wound during or following the procedure. For example, in many endoscopic procedures requiring catheterization, it is desirable to close an incision in the femoral artery following the catheterization. While some adhesives and coagulants are available for closing such incisions, it is often preferred to close the incision using traditional sutures. One problem created by the use of sutures during endoscopic procedures is that little room is available for tying or otherwise manipulating the suture. For this reason, it is often preferable to tie a suture knot outside the body and then run the knot to the artery (or other incision cite) using a knot pusher, thereby cinching the loop of suture and closing the incision.

Known knot pushers suffer from several problems. In some cases, knot pushers are complicated or unwieldy, making them difficult to use. In other cases, sutures may tend to slip out of grooves or recesses in knot pushers. When this happens, valuable time may be wasted recovering the knot or tying a new suture.

SUMMARY OF THE INVENTION

A knot pusher according to the present invention includes a longitudinal member having a proximal end and a distal end, the longitudinal member having a suture slit extending along a portion of the longitudinal member from the distal end. In addition, the knot pusher includes a latch coupled to the distal end of the longitudinal member. The latch is movable between an extended position and a locking position, so that the latch obstructs a portion of the suture slit when in the locking position.

BRIEF DESCRIPTION OF THE DRAWINGS

FIG. 1 is a perspective view of an exemplary embodiment of a knot pusher according to the present invention.

FIG. 2 is a perspective view of the knot pusher of FIG. 1 in a second operative position.

FIG. 6 is a perspective view of a second exemplary embodiment of a knot pusher according to the present invention.

FIG. 7 is a perspective view of a third exemplary embodiment of a knot pusher according to the present invention.

FIG. 8 is a perspective view of a fourth exemplary embodiment of a knot pusher according to the present invention.

FIG. 9 is a perspective new of an exemplary clasp of a knot pusher according to the present invention.

FIG. 10 is a perspective view of a second exemplary clasp of a knot pusher according to the present invention.

DETAILED DESCRIPTION

Figure 3:
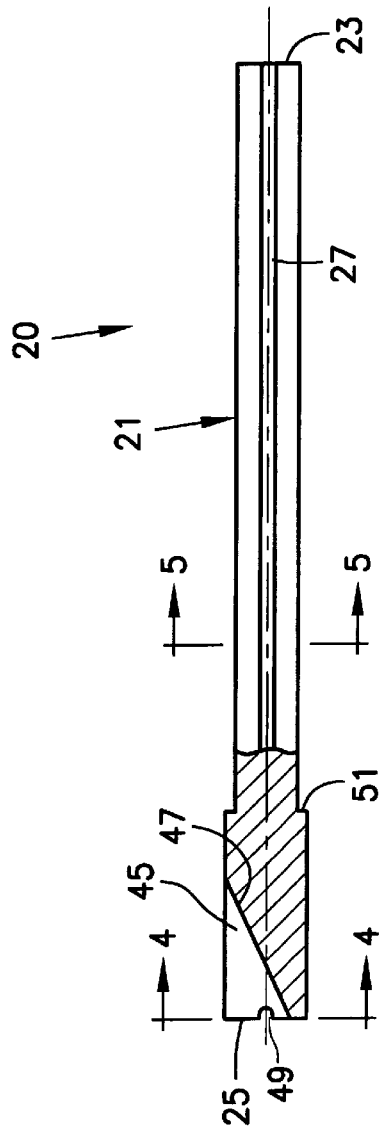
FIG. 3 is a partial cross-sectional side view of the knot pusher of FIG. 1.

As illustrated in FIG. 1, a knot pusher 20 according to the present invention includes a longitudinal member 21 having a proximal end 23 and a distal end 25; proximal generally designating a direction toward an operator (outside a patient). In general, knot pusher 20 includes a suture slit 45 extending proximally from distal end 25, and a latch 31 also disposed, at least in part, at distal end 25. Latch 31 is movable between an extended position, illustrated in FIG. 1, and a locking position, illustrated in FIG. 2. With latch 31 in the extended position, a length of suture 61 having a knot 63 may be drawn through suture slit 45, with contact between the distal end 25 and the knot 63 keeping knot 63 distal of lock pusher 20 by preventing knot 63 from entering the suture slit 45. Latch 31 may then be moved to the locking position to lock suture 61 within suture slit 45. Once suture 61 is retained securely with suture slit 45, the operator may run knot 63 down suture 61 by pushing knot 63 with distal end 25 of longitudinal member 21. Those skilled in the art will understand that knot 63 is "run down" the suture 61 by sliding the knot along the suture 61 decreasing the length of suture forming the loop 62 of suture 61.

In the exemplary embodiment of FIGS. 1 and 2, longitudinal member 21 is generally cylindrical in shape, although any suitable shape may be employed. For example, longitudinal member 21 could be oval or oblong in cross section. Longitudinal member 21 also may include, for example, at least one longitudinal groove 27 extending from distal end 25 along the length of longitudinal member 21. Preferably, longitudinal member 21 includes a pair of grooves 27 and 29, which may be disposed on opposite radial sides of longitudinal member 21.

This exemplary embodiment is illustrated in FIGS. 1 and 2. While grooves 27, 29 do not extend the full length of longitudinal member 21 in the Figures, such a configuration is suitable, if desired.

Latch 31 is coupled to longitudinal member 21 so that latch 31 is movable between the extended position of FIG. 1 and the locking position of FIG. 2. In the illustrated embodiment, latch 31 is formed from a length of wire, which may be any suitable material. Latch 31 may also be formed in any other suitable manner. Preferably, latch 31 includes at least one extension wire 33, and may have two extension wires 33, 35 which are, for example, slidably received in the grooves 27, 29, respectively. Extension wires 33, 35 are each connected, for example, at a distal end to a cross wire 37. Knot pusher 20 may also include a sleeve 41, which may be slid over longitudinal member 21 during construction of the device. Sleeve 41 may cover at least a portion of grooves 27, 29, to retain extensions wires 33, 35 within grooves 27, 29.

A handle 39 may also be provided, with handle 39 preferably being connected to at least one of the extension wires 33, 35. A second handle 39 may be provided, and may be connected, for example, to the other extension wire 33, 35. Handle 39 is preferably formed as a straight length of wire, and preferably extends out of groove 27 or 29 for manipulation by the operator. It is understood, however, that handle 39 could take numerous forms, for example a thumb loop, a rounded knob, or any other suitable form. In the illustrated embodiment, latch 31, including handle 39, is formed integrally as a single piece of wire, for example stainless steel wire, but latch 31 could be formed in separate units and later connected.

Latch 31 cooperates with suture silt 45 to retain a length of suture 61 within suture slit 45. Suture slit 45 may extend proximally along longitudinal member 21 from distal end 25. In general, suture slit is arranged to receive a suture 61 therethrough, but is sized to prevent any knot 63 in suture 61 from entering suture slit 45. In particular, suture slit 45 is preferably centered between grooves 27, 29, so that cross wire 37 is substantially transverse to suture slit 45 along distal end 25, as illustrated in the Figures. If desired, however, grooves 27, 29 and suture slit 45 could be arranged so that suture slit 45 and cross wire 37 intersect at any desired angle.

In general, latch 31 (for example cross wire 37), when in the locking position, preferably should obstruct or cover a portion of suture slit 45 along distal end 25. In this manner, suture 61 may be retained within suture slit 45 and be freely movable within suture slit 45, while knot 63 is held against distal end 25 of longitudinal member 21 as it is run down suture 61. In the illustrated arrangement, for example, suture slit 45 has, at distal end 25, a depth greater than the radius of the longitudinal member 21. In this exemplary arrangement, suture slit 45 extends through a center point of distal end 25. At the same time, cross wire 37 is arranged, for example, along a diameter of distal end 25 substantially perpendicular to the suture slit 45, so that when latch 31 is in the locking position, cross wire 37 obstructs suture slit 45 at the center point of distal end 25. This configuration provides sufficient room for suture 61 to slide through suture slit 45, and maintains knot 63 near the center of distal end 25.

In operation, latch 31, when in the locking position, retains suture 61 in suture slit 45 while knot pusher 20 cinches knot 63. In the illustrated embodiment, movement of latch 31 is limited by sleeve 41 at one end and by the proximal end of groove 27 or 29 (or both) at the other end. In particular, proximal end 43 of sleeve 41 forms a distal stop for handle 39 as it moves from the locking position to the extended position, while the proximal end of groove 27 or 29 forms a proximal stop. Of course, contact between the cross wire 37 and the distal end 25 will also limit the movement of the latch 31 proximally.

To use knot pusher 20, an operator may first draw suture 61 within latch 31 with the latch 31 in the extended position, placing suture 61 in a position in which latch 31 may be used to lock suture 61 within suture slit 45. In the exemplary embodiment of FIGS. 1 and 2, placing suture 61 within latch 31 includes drawing a proximal end of suture 61 through the space formed between latch 31 and distal end 25. This allows suture 61 to be easily threaded into suture slit 45. The operator may then move latch 31 to the locking position, for example by drawing handle 39 proximally. With suture 61 locked within suture slit 45 by latch 31, the operator may then run knot 63 down suture 61 by advancing the distal end 25 of the longitudinal member 21 distally, thereby pushing knot 63 along the suture 61 and cinching the loop 62.

Figure 5:
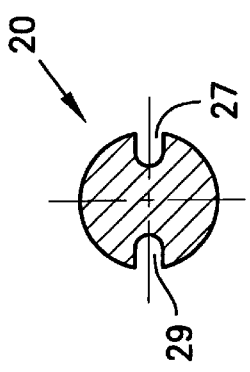
FIG. 5 is a cross-sectional view of the knot pusher of FIG. 1, taken along line 5—5 of FIG. 3.
Figure 4:
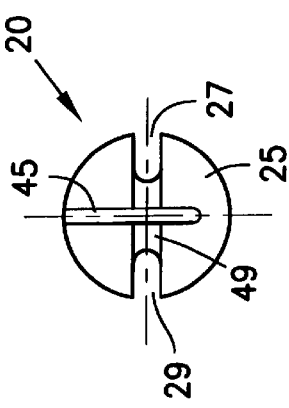
FIG. 4 is a cross-sectional view of the knot pusher of FIG. 1, taken along line 4—4 of FIG. 3.

FIGS. 3 to 5 illustrate additional features of an exemplary knot pusher 20 according to the present invention. As can be seen in FIG. 3, suture slit 45 is preferably formed so that its depth decreases as suture slit 45 extends in the proximal direction. In particular, the depth of suture slit 45 may decrease linearly as suture slit 45 extends proximally, so that the lower edge 47 of suture slit 47 forms a substantially straight line, at an angle to the axis of longitudinal member 21. Distal end 25 of longitudinal member 21 may also include a latch groove 49 to receive latch 31 when it is in the locking position. Latch 31 may then more securely retain suture 61, minimizing any chance that suture 61 or knot 63 may slip out of place. In addition, longitudinal member 21 may include an annular shoulder 51 facing the proximal direction. Annular shoulder 51 may provide a stop for sleeve 41 when sleeve 41 is placed over longitudinal member 21.

FIG. 7 shows another exemplary embodiment of a knot pusher 21 according to the present invention. In this embodiment, extension wires 27, 29 (if both are present) are primarily retained within longitudinal bores 53, 55. Longitudinal bores 53, 55 may be formed in longitudinal member 21, and may extend proximally from the distal end 25. At a point along longitudinal member 21, longitudinal bores 53, 55 may connect to longitudinal grooves 27, 29, which may extend proximally from longitudinal bores 53, 55. Grooves 27, 29 allow, for example, handle 39 to extend from longitudinal member 21, and allow handle 39 to be manipulated proximally and distally to actuate latch 31. Shoulder 51 may be provided, in this embodiment, at the intersection of bores 53, 55 and grooves 27, 29. This provides for a simple construction of longitudinal member 21. In particular, a drilling element may be employed to form bore 53 and groove 27 at the same time, as well as bore 55 and groove 29 at the same time.

The exemplary embodiment of FIG. 7 also includes a suture retention slit 57. Retention slit 57 is preferably formed at proximal end 23 of longitudinal member 21. Retention slit 57 may be sized and shaped to frictionally retain a segment of suture 61 placed therein, and is preferably chamfered for this purpose. The frictional retention of suture 61 may assist in cinching knot 63 and generally closing a wound. After loop 62 has been cinched by knot pusher 20, suture 61 may be inserted into retention slit 57 with knot pusher 20 still applying pressure to knot 63. In this manner, knot pusher 20 and knot 63 may be maintained in position, applying pressure to the wound or closure site, until hemostasis is achieved at the site.

FIG. 8 illustrates further exemplary features of the present invention. To further assist an operator, a knot pusher 20 according to the present invention may include a latch spring 59. In general, latch spring 59 may be coupled to longitudinal member 21 and latch 31 to bias latch 31 to the locking position. In the illustrated embodiment, latch spring 59 is disposed around longitudinal member 21 between handle 39 and distal end 43 of sleeve 41. In use, an operator may then urge latch 31 to the extended position, draw the proximal end of suture 61 within latch 31, and then release latch 31 (e.g., release handle 39) to place latch 31 in the locking position. Knot pusher 20 may also include a knob 24 disposed at proximal end 23 of longitudinal member 21. Knob 24 is preferably formed of a different material, for example a softer material, than longitudinal member 21 to facilitate handling of knot pusher 20. If provided, knob 24 may include retention slit 57, described above.

A method for cinching a loop using a knot pusher according to the present invention includes drawing a proximal end of a length of suture 61 within latch 31 and through suture slit 45, so that knot 63 remains distal of the latch. That is, knot 63 is not drawn within latch 31. If latch spring 59 is provided, latch 31 may be moved to the extended position before suture 61 is drawn within latch 31. Next latch 31 may be moved to the locking position to lock suture 61 within the suture slit 45. If latch spring 59 is present, latch 31 may simply be released by the operator to move latch 31 to the locking position. If handle 39 is present, movement of latch 31 may be achieved by movement (or release) of handle 39. With suture 61 locked in suture slit 45, the operator may then run knot 63 distally down the length of suture 61 using distal end 25 of knot pusher 20. If retention slit 57 is also present, the length of suture 61 may be inserted into retention slit 57 to retain knot pusher 20 in position along suture 61, preferably with knot pusher 20 applying pressure to knot 63 and the closure site or wound.

The device according to the present invention has been described with respect to several exemplary embodiments. It can be understood, however, that there are many other variations of the above-described embodiments which will be apparent to those skilled in the art, even where elements have not explicitly been designated as exemplary. For example, extension wire 33 could extend through the entire length of longitudinal member 21 and from proximal end 23, so that handle 39 is maintained proximal of longitudinal member 21. It is understood that this and other modifications are within the teaching of the present invention, which is to be limited only by the claims appended hereto.

What is claimed is:

1. A knot pusher, comprising:
   a longitudinal member extending from a proximal end to a distal end;
   a suture slit extending proximally along a portion of the longitudinal member from the distal end; and
   a latch coupled to the distal end, the latch being movable between an extended position and a locking position, wherein the latch includes an extension wire, a proximal end of the extension wire being coupled a handle and a distal end thereof being coupled to a cross wire so that, when the handle is moved proximally, the latch moves to the locking position with the cross wire obstructing a portion of the suture slit.

2. The knot pusher according to claim 1, wherein the latch includes a cross wire, an extension wire, a distal end of the extension wire being connected to the cross wire, and a handle, the handle being coupled to the extension wire, so that when the handle is urged proximally, the latch moves to the locking position so that the cross wire obstructs the suture slit.

3. The knot pusher according to claim 1, wherein the longitudinal member has a longitudinal groove therein, the extension wire being disposed within the longitudinal groove and being movable therein, and the handle extending from the longitudinal groove.

4. The knot pusher according to claim 3, further comprising a sleeve disposed around at least a portion of the longitudinal member, the sleeve covering at least a portion of the longitudinal groove to retain the extension wire within the longitudinal groove.

5. The knot pusher according to claim 4, wherein:
   the latch includes first and second extension wires each connected to the cross wire, and first and second handles each connected to a corresponding one of the first and second extension wires;
   the longitudinal member includes first and second longitudinal grooves, each of the first and second extension wires being disposed within a corresponding one of the first and second longitudinal grooves; and
   the sleeve covers at least a portion of each of the first and second longitudinal grooves.

6. The knot pusher according to claim 4, further comprising a latch spring coupled to the longitudinal member and to the latch, the latch spring biasing the latch towards the locking position.

7. The knot pusher according to claim 6, wherein the latch spring is disposed around the longitudinal member between the sleeve and the handle, the latch urging the handle proximally.

8. The knot pusher according to claim 1, wherein the suture slit has a depth at least as great as a radius of the longitudinal member at the distal end, the depth decreasing linearly as the suture slit extends proximally.

9. The knot pusher according to claim 1, the longitudinal member having a retention slit therein at the proximal end, the retention slit being sized to frictionally retain a section of suture.

10. The knot pusher according to claim 9, wherein the retention slit is chamfered.

11. The knot pusher according to claim 1, wherein the longitudinal member has a longitudinal bore extending proximally from the distal end, and a longitudinal groove extending proximally from the longitudinal bore, the extension wire being disposed within the longitudinal bore, and the handle extending from the longitudinal groove.

12. The knot pusher according to claim 11, wherein:
   the latch includes first and second extension wires each connected to the cross wire, and first and second handles each connected to a corresponding one of the first and second extension wires; and
   the longitudinal member includes first and second longitudinal bores and first and second longitudinal grooves, each of the first and second extension wires being disposed within a corresponding one of the first and second longitudinal bores, and each of the first and second manipulation ports extending from a corresponding one of the first and second longitudinal grooves.

13. The knot pusher according to claim 11, further comprising a latch spring coupled to the longitudinal member and to the latch, the latch spring biasing the latch towards the locking position.

14. The knot pusher according to claim 11, wherein the suture slit has a depth at least as great as a radius of the longitudinal member at the distal end, the depth decreasing linearly as the suture slit extends proximally.

15. The knot pusher according to claim 11, the longitudinal member having a retention slit therein at the proximal end, the retention slit being sized to retain a section of suture.

16. The knot pusher according to claim 15, wherein the retention slit is chamfered.

17. The knot pusher according to claim 11, further including a knob disposed at the proximal end of the longitudinal member.

18. The knot pusher according to claim 17, wherein the knob is formed from a first material and the longitudinal member is formed from a second material, the first material being softer than the second material.

19. The knot pusher according to claim 18, wherein the knob includes a retention slit, the retention slit being sized to retain a length of suture.

20. A method of cinching a loop in a length of suture using a knot pusher, the knot pusher including a longitudinal member having a suture slit extending along a portion thereof proximally from a distal end thereof, and a latch coupled to the distal end of the longitudinal member, the latch being movable between an extended position in which the latch is separated from the distal end and a locking position in which the latch is adjacent to the distal end obstructing a portion of the suture slit, the method comprising:
   drawing a proximal end of the length of suture with a knot formed therein proximally past the latch through the suture slit, so that the knot remains distal of the latch;
   positioning the latch in the locking position to lock the suture within the suture slit; and
   moving the knot pusher distally to push the distal end against the knot thereby moving the knot distally down the length of suture.

21. The method according to claim 20, wherein the latch includes a handle disposed near the proximal end of the longitudinal member, and wherein moving the latch into the locking position includes drawing the handle proximally.

22. The method according to claim 20, wherein the knot pusher further includes a latch spring biasing the latch in a proximal direction, further comprising, before drawing the proximal end of the length of suture through the suture slit, urging the latch distally to the extended position, and wherein moving the latch to the locking position includes releasing the latch.

23. The method according to claim 20, wherein the longitudinal member further includes a retention slit at the proximal end, further comprising inserting the length of suture into the retention slit to retain the knot pusher in a position along the length of suture.

24. The method according to claim 20, wherein the knot pusher further includes a knob disposed at the proximal end of the longitudinal member, the knob having a retention slit, further comprising inserting the length of suture into the retention slit to retain the knot pusher in a position along the length of suture.

25. A knot pusher, comprising:

a longitudinal member having a suture slit extending along a portion of the longitudinal member from a distal end thereof; and a latch movably coupled to the distal end for movement between an extended position in which the latch is extended distally away from the distal end and a locking position in which the latch is adjacent to the distal end to obstruct a portion of the suture slit.

26. A knot pusher, comprising:

a longitudinal member having a suture slit extending along a portion of the longitudinal member from a distal end thereof; and a latch movably coupled to the distal end for movement between an extended position in which the latch is extended distally away from the distal end and a locking position in which the latch obstructs a portion of a distal-most end of the suture slit.

* * * * *